US012758130B2

(12) United States Patent
Shi et al.

(10) Patent No.: US 12,758,130 B2
(45) Date of Patent: Oct. 13, 2026

(54) SIMPLE HEAD PRESSING TYPE DISPOSABLE SAFETY LANCET

(71) Applicant: STERILANCE MEDICAL (SUZHOU) INC., Suzhou (CN)

(72) Inventors: Guoping Shi, Suzhou (CN); Anthony Scott Horstman, Suzhou (CN); Xiangsheng Wang, Suzhou (CN); Jinquan Zhang, Suzhou (CN)

(73) Assignee: STERILANCE MEDICAL (SUZHOU) INC., Suzhou (CN)

( * ) Notice: Subject to any disclaimer, the term of this patent is extended or adjusted under 35 U.S.C. 154(b) by 272 days.

(21) Appl. No.: 18/696,166

(22) PCT Filed: Sep. 27, 2022

(86) PCT No.: PCT/CN2022/121883
§ 371 (c)(1),
(2) Date: Mar. 27, 2024

(87) PCT Pub. No.: WO2023/051555
PCT Pub. Date: Apr. 6, 2023

(65) Prior Publication Data
US 2024/0398301 A1 Dec. 5, 2024

(30) Foreign Application Priority Data
Sep. 28, 2021 (CN) .......................... 202111144739.6

(51) Int. Cl.
*A61B 5/151* (2006.01)

(52) U.S. Cl.
CPC ...... *A61B 5/15142* (2013.01); *A61B 5/15113* (2013.01)

(58) Field of Classification Search
None
See application file for complete search history.

(56) References Cited

U.S. PATENT DOCUMENTS 9,131,954 B2 9/2015 Hong
2012/0215246 A1* 8/2012 Hyoue ............. A61B 5/150259 606/182

(Continued)

FOREIGN PATENT DOCUMENTS

CN 103179903 A 6/2013
CN 207734167 U 8/2018

(Continued)

OTHER PUBLICATIONS

Dec. 7, 2022 International Search Report issued in International Patent Application No. PCT/CN2022/121883.

*Primary Examiner* — Etsub D Berhanu
(74) *Attorney, Agent, or Firm* — Oliff PLC

(57) ABSTRACT

A safety lancet includes a housing, a needle core, a pusher and a launching spring, the front end of the needle core having a protective rod, the side of the needle core having an elastic arm having a protrusion; a sliding platform is provided for the protrusion on the inner wall of the housing, and the front end face of the sliding platform is the triggering surface for triggering launching the lancet, and the tabletop of the sliding platform is a sliding surface in the length direction of the lancet; the distance of the decoupling point of the projection relative to the center of the lancet is greater than or equal to the distance of the sliding surface relative to the center of the lancet; a stopper is on the protection rod, and corresponding to the stopper a second limit surface is on the inner wall of the pusher.

10 Claims, 11 Drawing Sheets

(56) References Cited

U.S. PATENT DOCUMENTS

| | | | | |
|---|---|---|---|---|
| 2013/0066353 | A1 | 3/2013 | Hong | |
| 2016/0022177 | A1 * | 1/2016 | Shi | A61B 5/150022 606/182 |
| 2019/0053746 | A1 * | 2/2019 | Shi | A61B 5/15117 |
| 2021/0169386 | A1 | 6/2021 | Shi | |

FOREIGN PATENT DOCUMENTS

| | | | | |
|---|---|---|---|---|
| CN | 113995407 | A | 2/2022 | |
| JP | 2018-079126 | A | 5/2018 | |
| JP | 2019-208748 | A | 12/2019 | |
| WO | WO-2019161787 | A1 * | 8/2019 | A61B 5/15144 |

* cited by examiner

SIMPLE HEAD PRESSING TYPE DISPOSABLE SAFETY LANCET

FIELD

The present invention relates to medical blood collection devices, in particular to a simple head pressing type disposable safety lancet (also known as blood collection needle). This lancet has a simple structure, good safety, reliable operation, low cost as a disposable product, with market competition potential.

BACKGROUND OF THE INVENTION

Among the medical blood collection devices, the disposable safety lancet, characterized by its small size, safe use and convenient operation, is welcomed by healthcare personnel and patients, and is currently used in large quantities in various medical institutions as well as among diabetic patients. This kind of lancet has an ejection mechanism, with compact structure and overall disposable use, which is both safe and convenient, and thus has a strong potential for market development.

At present, there are various structural forms of disposable blood collection devices on the market, but according to triggering form, there are two types. The first one is the head pressing type disposable safety lancet, and the second one is the tail pressing type disposable safety lancet. The so-called head pressing type and tail pressing type refer to whether the component that triggers the ejection of lancet is located at the head or tail. From the current overall development trend of blood collection devices products, the market acceptance has largely shifted towards a focus on low product prices, simple structure, and reliable operation. Among the above two types of blood collection devices, the head press type disposable safety lancet has a simpler structure, lower cost, and greater market potential.

Chinese patent CN103179903A disclosed an invention patent application titled "Safety lancet having a fail-safe reuse preventing function" on Jun. 26, 2013. It relates to head pressing type disposable safety lancet, with typical representative significance, and its basic structure mainly includes four major parts, namely, housing, needle core, pusher and launching spring, which not only has fewer parts and components, low manufacturing cost, but also has good working reliability. However, there is an obvious safety defect, that is, in the process of delivery and use due to vibration and accidental touching of the pusher in the head of lancet will easily lead to false triggering, which will not only lead to the premature failure of disposable lancet product, but also produce accidental injuries (e.g., piercing the finger).

In view of this, while retaining the advantages of head pressing type disposable lancet with fewer parts, low manufacturing cost and good working reliability, how to solve the safety problem of its false triggering is the subject of research of the present invention.

Content of the Invention

In view of the above deficiencies of existing technologies, the present invention provides a simple head pressing type disposable safety lancet, the purpose of which is to solve the safety problem caused by the original ejection structure due to being easily triggered by mistake.

In order to achieve the above objectives, the technical solutions adopted in the present invention are:

A simple head pressing type disposable safety lancet, including a housing, a needle core, a pusher and a launching spring, the direction pointed by needle tip of lancet defined as the front of the lancet; The front end of the needle core is equipped with a protective rod, and the side of the needle core is equipped with an elastic arm.

The elastic arm is provided with a first blocking surface and a resisting surface, a second blocking surface is provided on the pusher corresponding to the first blocking surface, and the second blocking surface cooperates with the first blocking surface in restricting a forward movement of the needle core in relation to the pusher; A triggering surface is provided on the inner wall of the housing corresponding to the resisting surface, the triggering surface cooperating with the resisting surface to force the elastic arm to bend towards inner side.

A first limiting surface is set on the outer side of the pusher, a locking bump is provided on the inner wall of the housing corresponding to the first limiting surface, and the locking bump cooperates with the first limit surface to limit a forward movement of the pusher relative to the housing.

Its innovation lies in: A sliding platform is provided for the resisting surface on the inner wall of the housing, the front end face of the sliding platform is the triggering surface, and the tabletop of the sliding platform forms a sliding surface in a length direction of lancet.

The second blocking surface has a decoupling point that matches the first blocking surface on the elastic arm, and taken a needle body of the lancet as a center on a cross-section of the lancet, the distance between the decoupling point and the center is greater than or equal to the distance between the sliding surface and the center.

The protective rod is equipped with a stopper, the stopper equipped with a obstructing surface, and a second limit surface is set on the inner wall of the pusher corresponding to the obstructing surface, the second limit surface cooperating with the obstructing surface on the stopper to limit a forward movement of the needle core relative to the pusher.

The relevant content and changes of the above technical solution are explained as follows:

1. In the above solution, the "housing", "needle core", "launching spring" and "pusher" are the most basic structural parts of the press-type disposable lancet, of which basic functions are existing technologies (see China Patent CN103179903A).

2. In the above solution, the elastic arm is equipped with a protrusion, the front end face of the protrusion is the first blocking surface, and the rear end face of the protrusion is the resisting surface.

In an initial assembly state, the housing is sleeved outside the pusher, the front end of the pusher protrudes out of an opening at the front end of the housing, the needle core is located inside the housing and positioned in a slide way of the pusher, the protective rod at the front end of the needle core is located inside the pusher, the front end of the protective rod protrudes out of a needle-tip puncture hole at the front end of the pusher, and the launching spring acts in an ejection direction between the needle core and the housing; the launching spring is in a pre-compressed state, the pre-compressed state of the launching spring forcing the obstructing surface of the stopper on the protective rod against the the second limit surface of the pusher, and forcing the first limiting surface of the pusher against the locking bump of the housing simultaneously.

In the initial assembly state, the second blocking surface of the pusher is located in front of the protrusion of the elastic arm, and the triggering surface on the inner wall of the housing and the sliding surface are located behind the protrusion of the elastic arm, so that the protrusion is located between the second blocking surface and the sliding platform; When the protective rod or the pusher is accidentally triggered, triggering force forces the needle core to move backward relative to the housing, further compressing the launching spring, while the protrusion on the elastic arm slides backward along the triggering surface to the sliding surface, until it stops sliding, but when eliminating the triggering force, under an action of the launching spring, the protrusion on the elastic arm slides along the sliding surface forward to a position between the second blocking surface and the sliding platform, restoring to the initial assembly state.

3. In the above solution, the sliding surface may be a flat surface which is parallel to an ejection direction of lancet. The invention is not limited to this and it may also be a beveled surface or a curved surface.

4. In the above solution, the resisting surface is a straight surface or a beveled surface or a curved surface. The difference between a straight surface and a beveled surface is that the former is a plane toward the back of lancet, and the latter is a plane that is inclined with respect to the plane.

5. In the above solution, the triggering surface may be a triggering beveled surface, a triggering curved surface, or even a triggering straight surface, but when the triggering surface is a triggering straight surface, the resisting surface that cooperates with the triggering surface shall be a beveled surface or a curved surface.

6. In the above solution, the needle core is provided with an impact surface, which is oriented towards the front of the lancet, corresponding to the impact surface, the pusher is provided with a third limiting surface, which is oriented towards the rear of the lancet, and during the ejection process of the needle core, the impact surface cooperates with the third limiting surface to limit the puncture depth of the lancet.

7. In the above solution, corresponding to the stopper on the protective rod, a notch for the stopper to pass through is provided next to the needle-tip puncture hole of the pusher, and in the initial assembly state, the notch is located in a rotational position in which the stopper is rotated with the protective rod.

8. In the above solution, the lancet may also be provided with a twist cap or cover cap, the twist cap or cover cap being set on the head of the pusher in the initially assembly state.

The design principle and conception of the present invention is as follows: in order to solve the safety problems brought by the ejection structure of the original head-pressing disposable safety lancet due to the fact that it is easy to be triggered by mistake, the present invention utilizes the protective rod in the original lancet as well as the structure of the elastic arm used for locking and triggering the needle core, purposefully improved and designed.

Specifically, it is reflected in the following aspects: firstly, a sliding platform is set up on the inner wall of the housing for the elastic arm on the needle core, the front end face of the sliding platform is used to trigger the triggering surface of the lancet, and the tabletop of the sliding platform is a sliding surface in the length direction of the lancet (in FIG. 13, the sliding platform is an inverted platform, labeled as 15). The function and effect of the sliding surface is to ensure that the protrusion temporarily slides along the sliding surface and stays on the platform in case of accidental triggering. Once the triggering force is eliminated, it immediately returns to its initial position under the action of the launching spring.

Secondly, the distance between the second blocking surface (used to block and lock the protrusion) set on the pusher and the center of the lancet should be designed to be greater than or equal to the distance between the sliding surface and the center of the lancet. In other words, the distance between the protruding decoupling point and the center of the blood collection device is designed to be greater than or equal to the distance between the sliding surface and the center of the blood collection device. The center of the lancet refers to the center of the needle body on the cross-section of the lancet. This design and requirement is to ensure that after removing the protective rod, the protrusion which is triggered by the triggering surface will no longer slides on the sliding platform, but smoothly detach from the second blocking surface to form an ejection. If the distance between the second blocking surface and the center of the lancet is less than the distance between the sliding surface and the center of the lancet, detachment cannot be achieved.

Thirdly, a stopper (obstructing surface) is set on the protective rod, and a second limit surface is set on the inner wall of the pusher. The second limit surface, in conjunction with the stopper (obstructing surface), limits the forward movement of the needle core relative to the pusher.

In this scheme, the design utilizes the connection relationship between the protective rod and the pusher to avoid accidental triggering through the coordination of the second limit surface and the stopper (obstructing surface). That is, without removing the protective rod, neither the protective rod nor the pusher can truly trigger the ejection structure of the lancet. In addition, the combination of the sliding platform and the launching spring allows the elastic arm to return to its initial assembly position after accidental triggering, ultimately restoring the lancet to its original initial assembly state. From this, it can be seen that the present invention not only retains the advantages of a head press disposable lancet with fewer components (only 4 components are needed), low manufacturing cost, and good working reliability, but also solves the safety problems of being easily triggered by errors. In summary, the present invention has a clever design concept, fewer components, good safety, low cost, outstanding innovative effect, outstanding substantive characteristics and significant technological progress, being a lancet product with market competition potential.

The symbols in the above drawings are described below:

1. housing; 11. locking bump; 12. triggering surface; 13. spring-connecting post; 14. guiding bevel; 15. sliding platform; 16. sliding surface; 2. needle core; 21. stopper; 22. elastic arm; 23. protrusion; 24. first blocking surface; 25. resisting surface; 26. protective rod; 27. spring hook; 28. needle body; 29. impact surface; 3. pusher; 31. second blocking surface; 32. third limiting surface; 33. needle core running limit track; 34. needle-tip puncture hole; 35. blood collection end face; 36. first limiting surface; 37. second limit surface; 38. notch; 4. launching spring; 5. twist cap.

MODE OF CARRYING OUT THE INVENTION

The invention is further described below in connection with drawings and embodiments:

Embodiment: A Simple Head Pressing Type Disposable Safety Lancet

Figure 1:
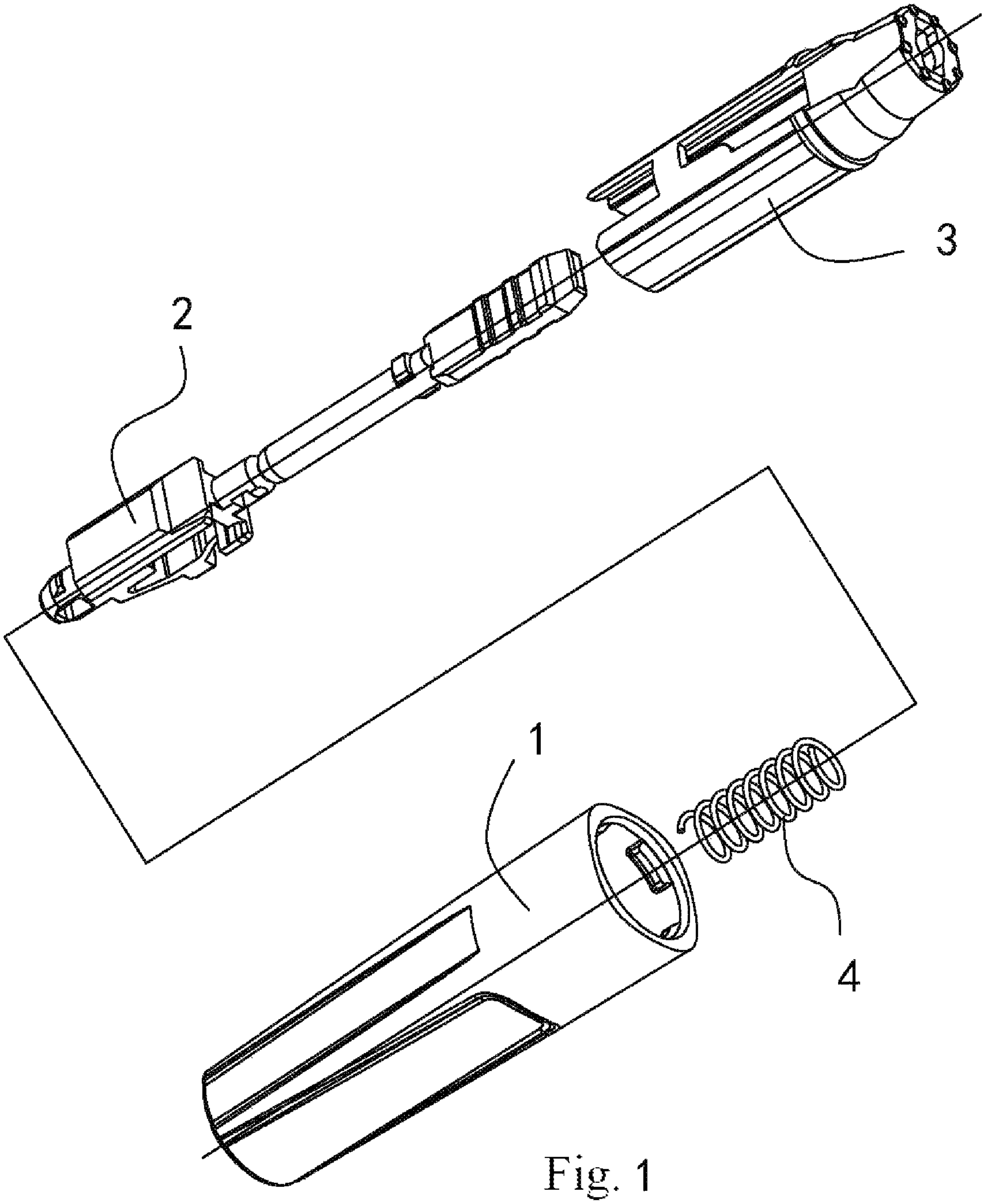
FIG. 1 is a three-dimensional sectional view of the lancet in an embodiment of the present invention.
Figure 2:
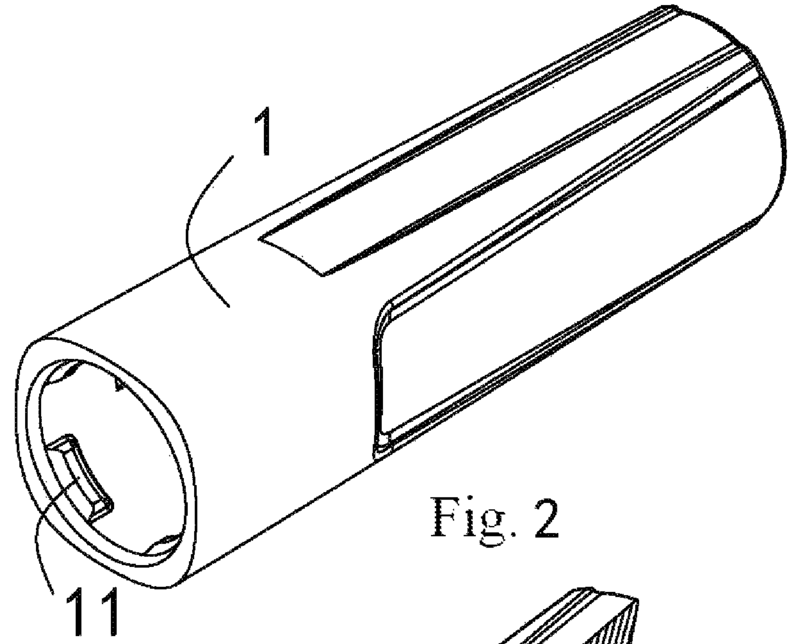
FIG. 2 is a three-dimensional view of the housing of an embodiment of the present invention.

As shown in FIGS. 1-15, the lancet includes a housing 1, a needle core 2, a pusher 3, and a launching spring 4 (see FIG. 1):

A protective rod 26 is provided at the front end of the needle core 2 (see FIGS. 5-7), the protective rod 26 covers the needle tip of the head of the needle body 28, and the connection between the protective rod 26 and the needle core 2 is provided with a disconnecting portion (see FIGS. 5-7) to allow for fracture at the disconnecting portion when the protective rod 26 is twisted. The disconnecting portion may be a constriction neck structure, a notch, a cut, or even a sleeve structure over the needle core 2, etc., with the constriction neck shown in FIGS. 5-7 of this embodiment.

Figure 5:
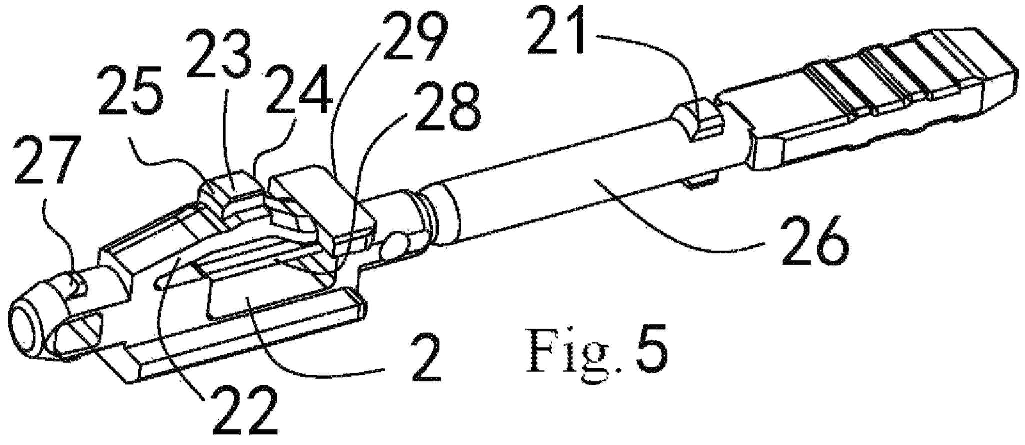
FIG. 5 is a first perspective stereoscopic view of the needle core in an embodiment of the present invention.
Figure 6:
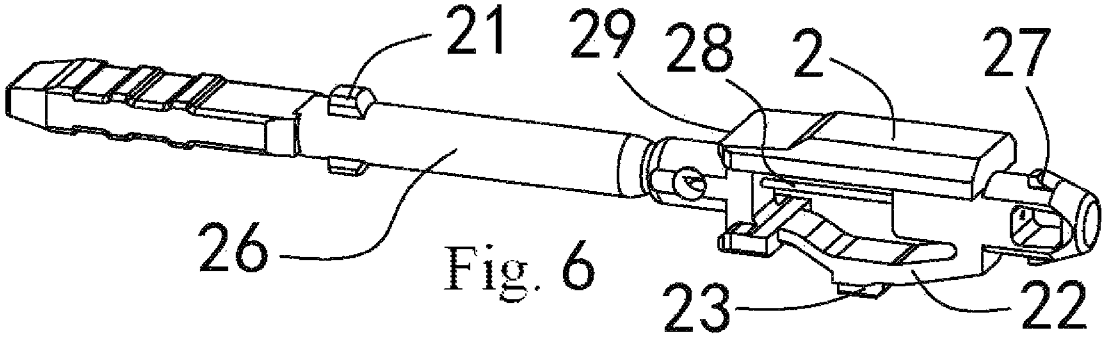
FIG. 6 is a second perspective stereoscopic view of the needle core in an embodiment of the present invention.
Figure 7:
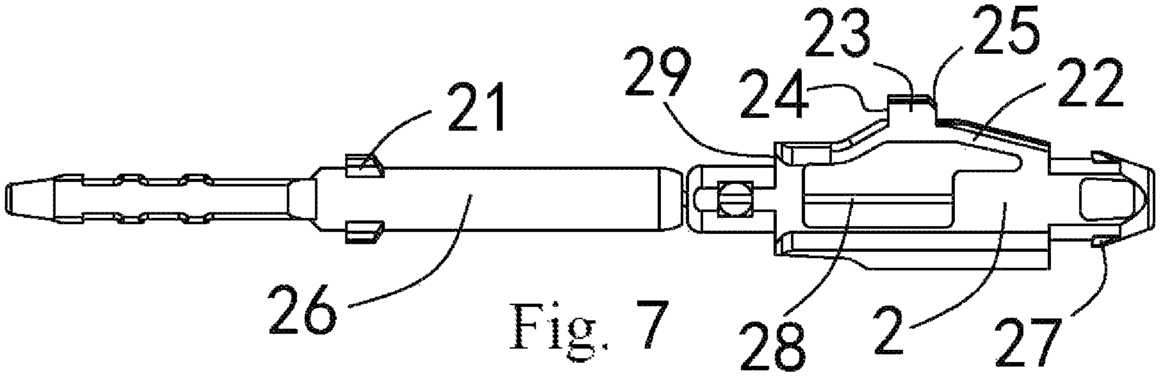
FIG. 7 is a main view of the needle core in an embodiment of the present invention.
Figure 8:
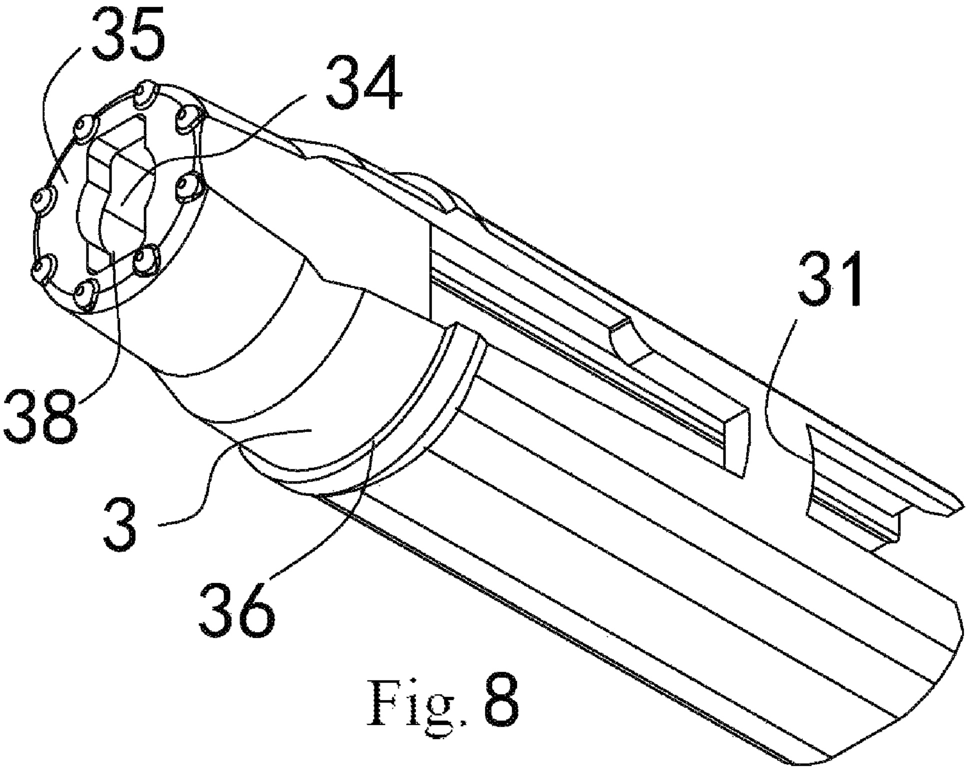
FIG. 8 is a first perspective stereoscopic view of the pusher in an embodiment of the present invention.
Figure 9:
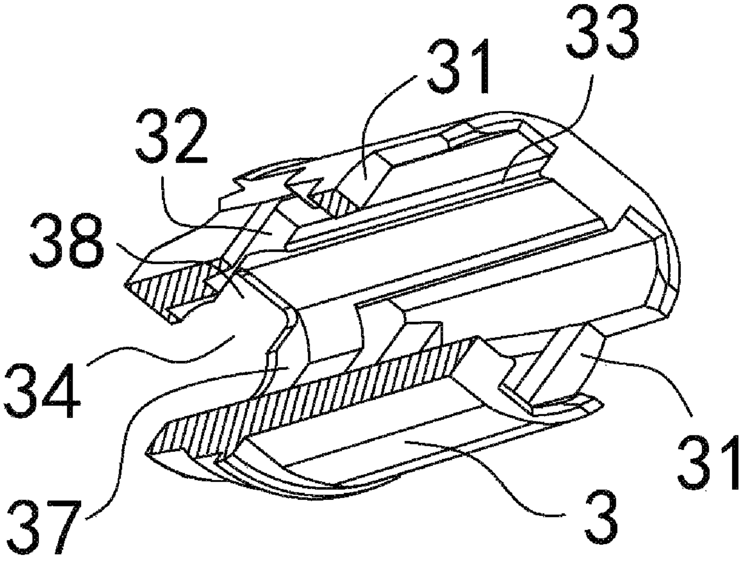
FIG. 9 is a three-dimensional sectional view of the pusher in an embodiment of the present invention.
Figure 10:
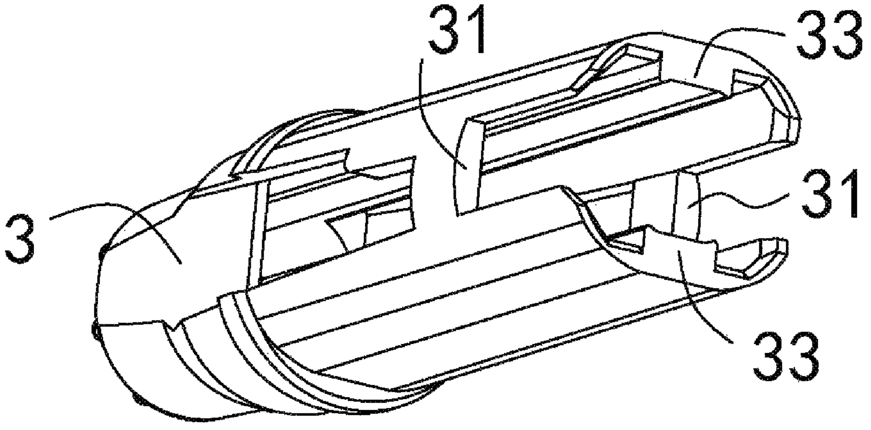
FIG. 10 is a second perspective stereoscopic view of the pusher in an embodiment of the present invention.
Figure 11:
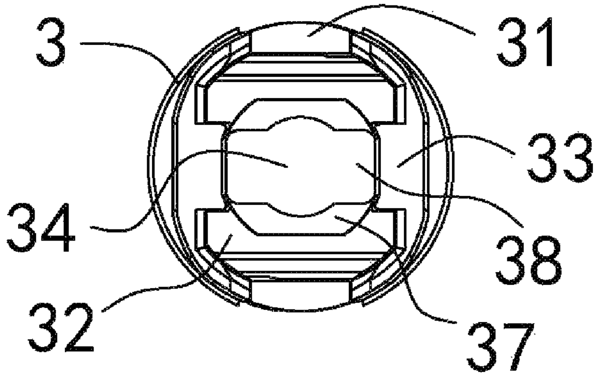
FIG. 11 is a left view of the pusher in an embodiment of the present invention.
Figure 12:
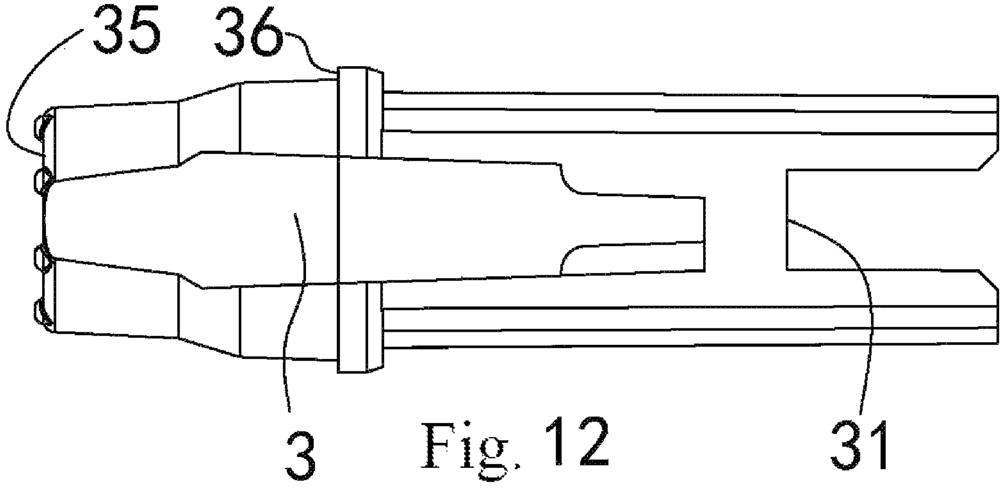
FIG. 12 is a main view of the pusher in an embodiment of the present invention.

The needle core 2 is provided with a elastic arm 22 on its side (see FIGS. 5-7), which is of an arching elastic arm structure, and the elastic arm 22 is provided with a protrusion 23 (see FIGS. 5-7). The direction pointed by needle tip of lancet defined as the front of the lancet, a first blocking surface 24 is provided at the front end of protrusion 23 (see FIG. 7), and a resisting surface 25 is provided at the rear end of protrusion 23 (see FIG. 7). The resisting surface 25 is beveled (see FIGS. 5 and 7).

Figure 13:
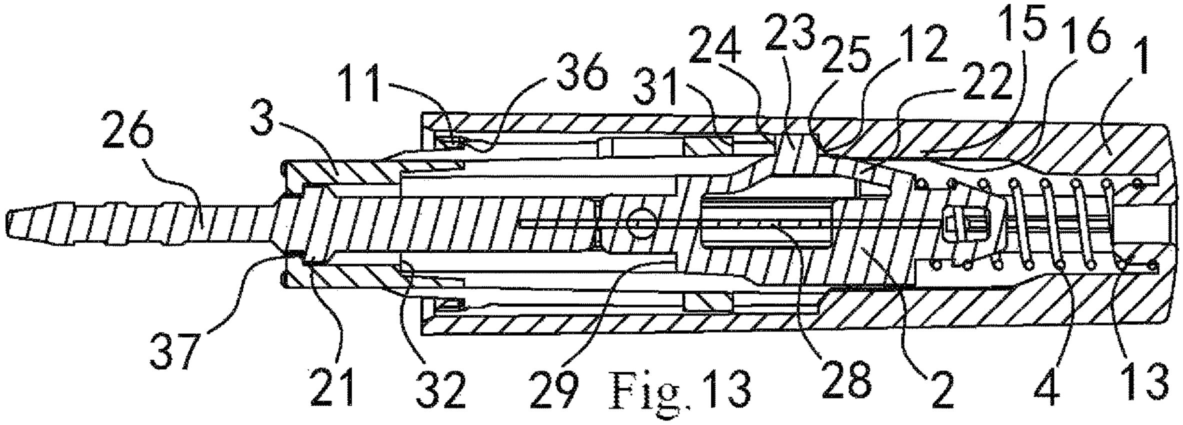
FIG. 13 is a sectional view of the initial assembly state of an embodiment of the present invention.

The first blocking surface 24 faces forward of the lancet (in the initial assembly state, as shown in FIG. 13), and the pusher 3 is provided with a second blocking surface 31 corresponding to the first blocking surface 24 (as shown in FIGS. 8-12). The second blocking surface 31 faces toward the rear of the lancet (in the initial assembly state, as shown in FIG. 13), and the second blocking surface 31 cooperates with the first blocking surface 24 to restrict the needle core 2 from moving forward relative to the pusher 3 (as shown in FIG. 13).

The resisting surface 25 is oriented towards the rear of the lancet (in the initial assembly state, see FIG. 13), and corresponding to the resisting surface 25 a triggering surface 12 is provided on the inner wall of the housing 1 (see FIGS. 3-4) which cooperates with the resisting surface 25 to force the elastic arm 22 to bend towards the inner side (see FIG. 13). The triggering surface 12 may be a triggering beveled surface, a triggering curved surface, or even a triggering straight surface, but when the triggering surface 12 is a triggering straight surface, the resisting surface 25 that cooperates with the triggering surface 12 shall be a beveled surface or a curved surface. Theoretically, at least one of the triggering surface 12 and the resisting surface 25 should be a beveled or curved surface.

A first limiting surface 36 is provided on the outer side of the pusher 3 (see FIG. 8 and FIG. 12), the first limiting surface 36 oriented towards the front of the lancet (in the initial assembly state, see FIG. 13), and corresponding to the first limiting surface 36 a locking bump 11 are provided on the inner wall of the housing 1 (see FIGS. 2 and 3), locking bump 11 in conjunction with the first limiting surface 36 limiting the forward movement of the pusher 3 with respect to the housing 1 (see FIG. 13).

Figure 3:
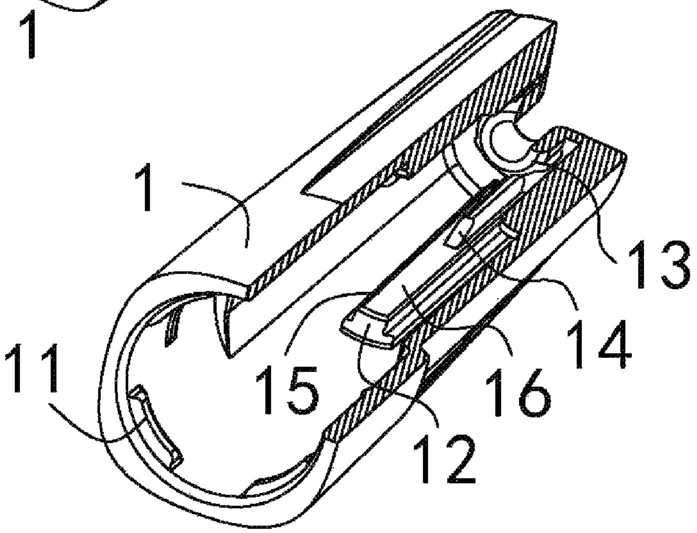
FIG. 3 is a three-dimensional sectional view of the housing of an embodiment of the present invention.
Figure 4:
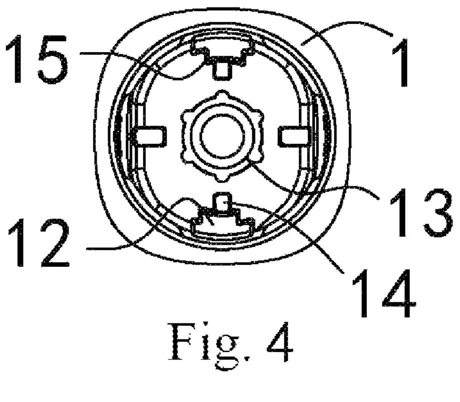
FIG. 4 is a front view of the bottom inside the housing of an embodiment of the present invention (viewed from the front end of the housing facing inward)

On the inner wall of the housing 1, a sliding platform 15 is provided against the protrusion 23 (see FIG. 3), the front end surface of this sliding platform 15 being the triggering surface 12 (see FIG. 3), and the table face of this sliding platform 15 being formed as a sliding surface 16 in the lengthwise direction of the lancet (see FIG. 3). The sliding surface 16 has the function and effect of ensuring that the protrusion 23 temporarily slides along the sliding surface 16 and stays on the sliding platform 15 in case of false triggering, and immediately recovers (returns) to the initial position under the action of the launching spring 4 as soon as the triggering force is removed. The sliding surface 16 is a flat surface which is parallel to the ejection direction of the lancet (see FIG. 13).

The second blocking surface 31 has a decoupling point cooperating with the first blocking surface 24 on the elastic arm 22, and taken a needle body 28 of the lancet as a center on a cross-section of the lancet, the distance between the decoupling point and the center is greater than or equal to the distance between the sliding surface 16 and the center (see FIG. 13). In other words, that is, the distance of the decoupling point at which the protrusion 23 cooperates with the first blocking surface 24 relative to the center of the lancet is designed to be greater than or equal to the distance of the sliding surface 16 relative to the center of the lancet. The center of the lancet is referred to herein as being centered on the needle body 28 in the cross-section of the lancet. This design and requirement is to ensure that after removing the protective rod, the protrusion 23 which is triggered by the triggering surface 12 will no longer slides on the sliding platform 15, but smoothly detach from the second blocking surface 31 to form an ejection. On the contrary, if the distance of the decoupling point on the second blocking surface 31 relative to the center of the lancet is less than the distance of the sliding surface 16 relative to the center of the lancet, decoupling cannot be achieved. Furthermore, it is evident from the unlocking process in FIGS. 19 and 20 that the decoupling point on the second blocking surface plays a significant role.

The protective rod 26 is provided with a stopper 21 (see FIGS. 5-7), which is provided with a obstructing surface (not labeled, the obstructing surface refers to the surface of the stopper 21 facing the front of the lancet in the initial assembly state).

The obstructing surface faces towards the front of the lancet, and corresponding to the obstructing surface, a second limiting surface 37 is provided on the inner wall of the pusher 3 (FIGS. 9 and 13), the second limiting surface 37 cooperates with the obstructing surface of the stopper 21 to restrict the forward movement of the needle core 2 with respect to the pusher 3 (see FIG. 13). The second limiting surface 37 cooperates with the blocking surface on the block 21 to limit the forward movement of the needle core 2 with respect to the pusher 3 (see FIG. 13). This design utilizes the connection between the protective rod 26 and the pusher 3 to avoid false triggering through the cooperation between the second limiting surface 37 and the stopper 21 (obstructing surface), i.e., neither the triggering of the protective rod 26 nor the pusher 3 can actually trigger the ejection structure of the lancet without removing the protective rod 26, together with the combination of the sliding platform 15 and the launching spring 4, so that the protrusion 23 on the elastic arm 22 will be restored to the initial assembly position again after the occurrence of false triggering, and ultimately the lancet will be restored to the original initial assembly state.

After the stopper 21 is provided on the protective rod 26, in order to solve the problem that the protective rod 26 can be easily twisted and removed, the stopper 21 on the protective rod 26 is correspondingly provided with a notch 38 that can be passed through by the stopper 21 next to the needle-tip puncture hole 34 of the pusher 3 (see FIG. 8), and the notch 38 is located in a rotational position in which the stopper 21 is rotated with the protective rod 26 in the initially assembly state. After rotating the protective rod 26, the stopper 21 aligned with the notch 38, the disconnecting portion between the protective rod 26 and the needle core 2 breaks, at which point the protective rod 26 can be withdrawn.

The needle core 2 is provided with an impact surface 29 (see FIGS. 5-7), which is oriented towards the front of the lancet, and corresponding to the impact surface 29 a third limiting surface 32 (see FIG. 9) is provided on the pusher 3, which is oriented towards the rear of the lancet (see FIG. 13), so that the impact surface 29 cooperates with the third limiting surface 32 to limit the puncture depth of the blood collection during the launching of the needle core 2 (see FIG. 13).

The initial assembly state and the use operation process of the embodiment of the present invention are as follows:

1. Initial Assembly State

Figure 14:
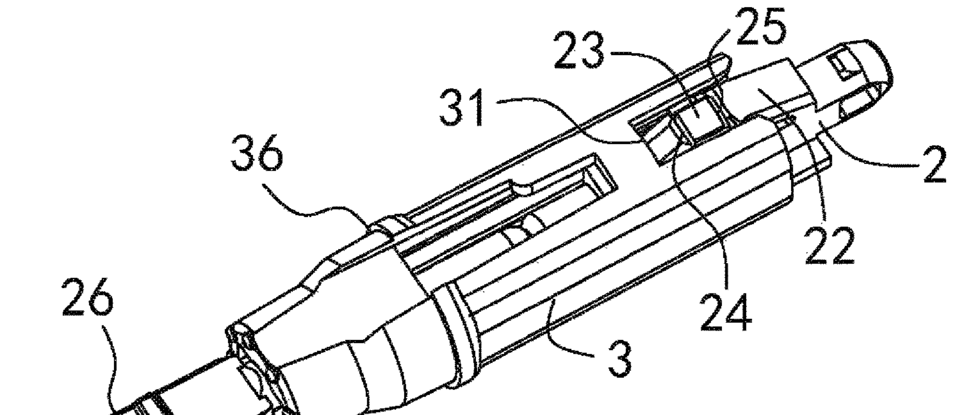
FIG. 14 is a three-dimensional view of the initial assembly state of the needle core and the pusher in an embodiment of the present invention.
Figure 15:
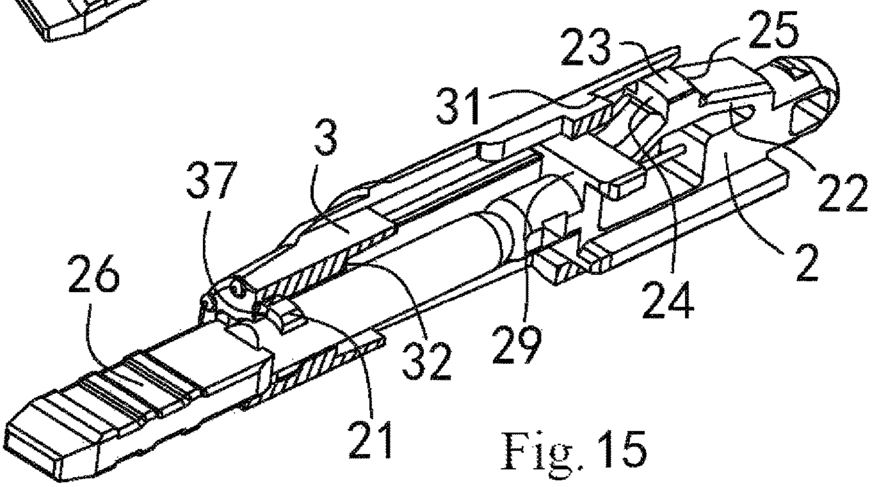
FIG. 15 is a three-dimensional sectional view of the initial assembly state of the needle core and the pusher in an embodiment of the present invention.

Referring to FIGS. 13-15, in the initial assembly state, the housing 1 is sleeved outside the pusher 3, the front end of the pusher 3 extends out from the opening of the front end of the housing 1, the needle core 2 is located in the housing 1 and positioned on the slide way of the pusher 3, the protective rod 26 at the front end of the needle core 2 is located in the pusher 3, the front end of the protective rod 26 extends out from the needle-tip puncture hole 34 at the front end of the pusher 3, and the launching spring 4 acts in the ejection direction between the needle core 2 and the housing 1. The launching spring 4 is in a pre-compressed state in the initial assembly state, the pre-compressed state of the launching spring 4 forcing the obstructing surface of the stopper 21 on the protective rod 26 to rest against the third limiting surface 37 of the pusher 3, and at the same time forcing the first limiting surface 36 of the pusher 3 to rest against the locking bump 11 of the housing 1.

In the initial assembly state (see FIGS. 13-15), the second blocking surface 31 of the pusher 3 is positioned in front of the protrusion 23 of the elastic arm 22, and the triggering surface 12 on the inner wall of the housing 1, as well as the sliding surface 16, are positioned behind the protrusion 23 of the elastic arm 22, so that the protrusion 23 is positioned between the second blocking surface 31 and the sliding platform 15. The second blocking surface 31, the first blocking surface 24, the resisting surface 25, and the triggering surface 12 are on the same movement path which is parallel to the ejection direction of the lancet.

2. State of Twisting the Protective Rod

Figure 16:
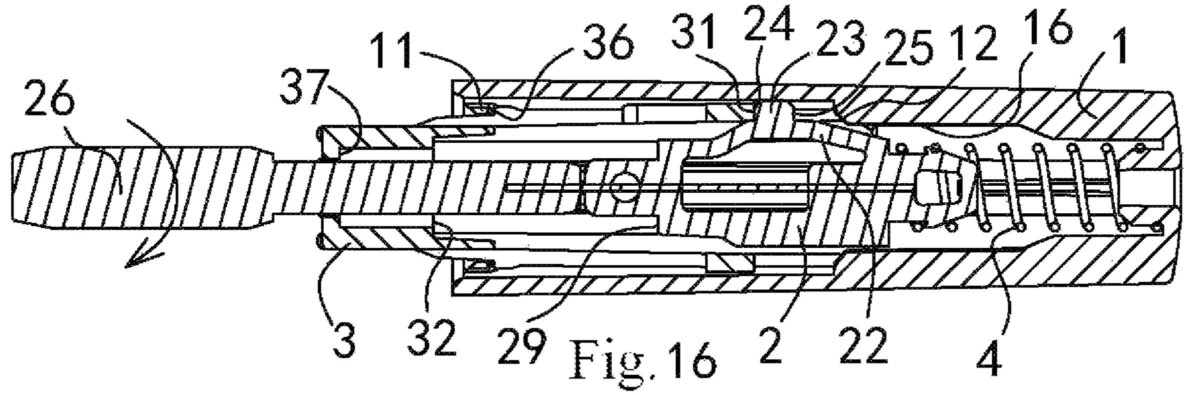
FIG. 16 is a sectional view of the state in which the protective rod is twisted in an embodiment of the present invention.

Referring to FIG. 16, the protective rod 26 is twisted (about 45-90 degrees) so that the block 21 on the protective rod 26 is aligned with the notch 38, and under the action of the launching spring 4, the needle core 2 is moved forward by 2 mm until the protrusion 23 on the elastic arm 22 of the needle core 2 is limited by the second blocking surface 31 on the pusher 3 and then stops moving (see FIG. 16).

3. State of Pending Ejection

Figure 17:
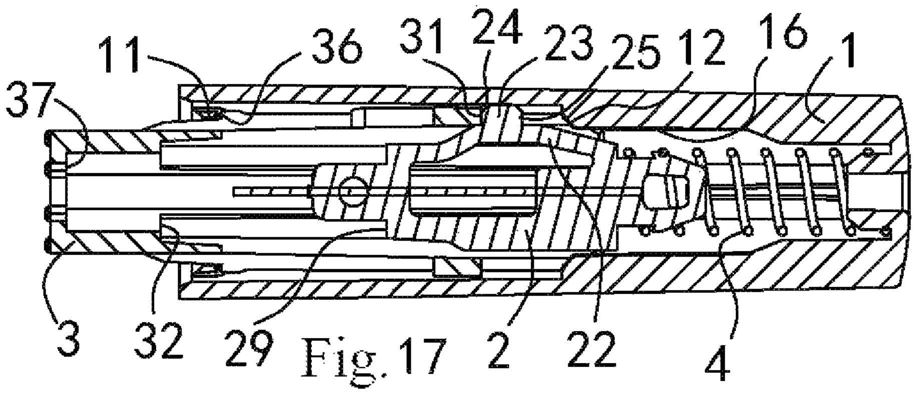
FIG. 17 is a sectional view of the state to be launched in an embodiment of the present invention.
Figure 18:
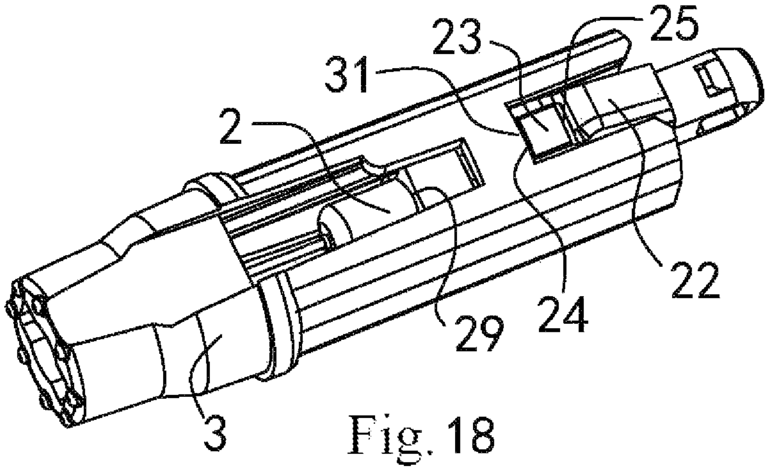
FIG. 18 is a three-dimensional view of the state to be launched in an embodiment of the present invention.

As shown in FIGS. 17 and 18, the protective rod 26 is continued to be twisted and the disconnecting portion between the protective rod 26 and the needle core 2 is broken, and then the protective rod 26 is removed, at which time the first blocking surface 24 on the protrusion 23 collides with the second blocking surface 31 on the pusher 3, and the needle core 2 is locked to the pusher 3.

4. State of Pressing the Pusher (I)

Figure 19:
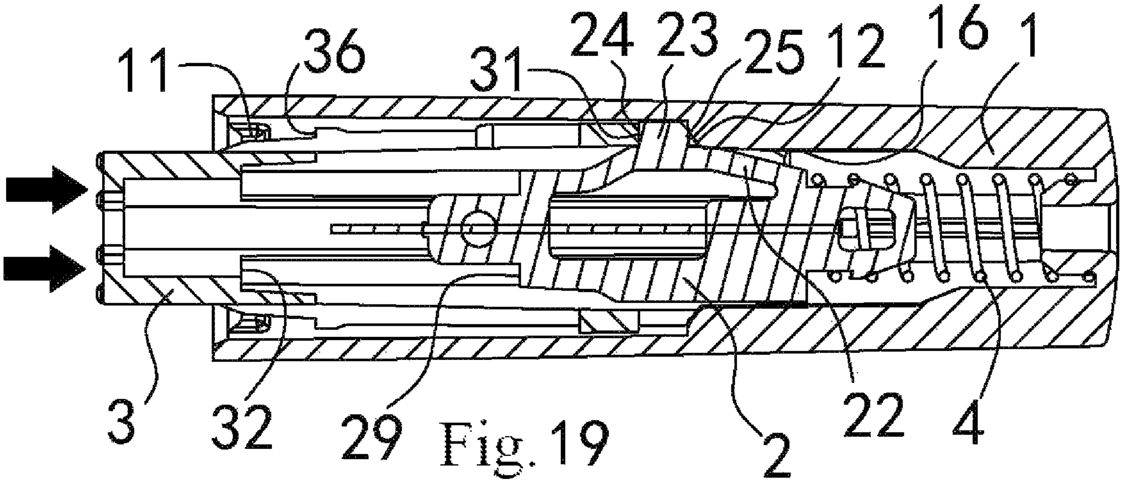
FIG. 19 is a sectional view of the pressed state (I) of the pusher in an embodiment of the present invention.

Referring to FIG. 19, pressing the front end of the pusher 3 (see the arrow in FIG. 19), the pusher 3 drives the needle core 2 backward through the cooperation of the second blocking surface 31 and the first blocking surface 24, at which time the protrusion 23 on the elastic arm 22 of the needle core 2 comes into contact with the triggering surface 12 on the inner wall on the housing 1.

5. State of Pressing the Pusher (II)

Figure 20:
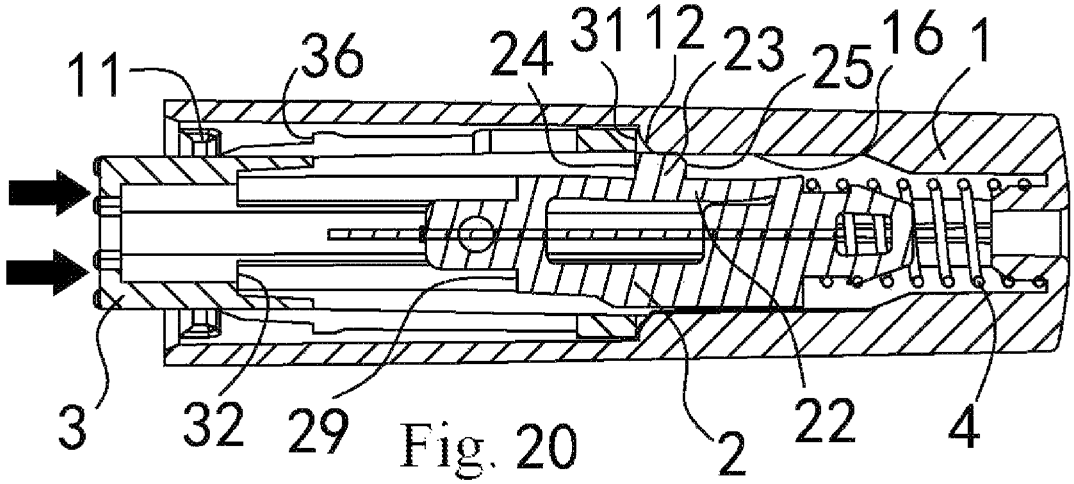
FIG. 20 is a sectional view of the pressed state (II) of the pusher in an embodiment of the present invention.

Referring to FIG. 20, continuing to press the front end of the pusher 3, the pusher 3 drives the needle core 2 to continue to move backward, and when the protrusion 23 on the elastic arm 22 of the needle core 2 crosses the second blocking surface 31 on the pusher 3, the needle core 2 is unlocked.

6. State of being Launched for Blood Collection

Figure 21:
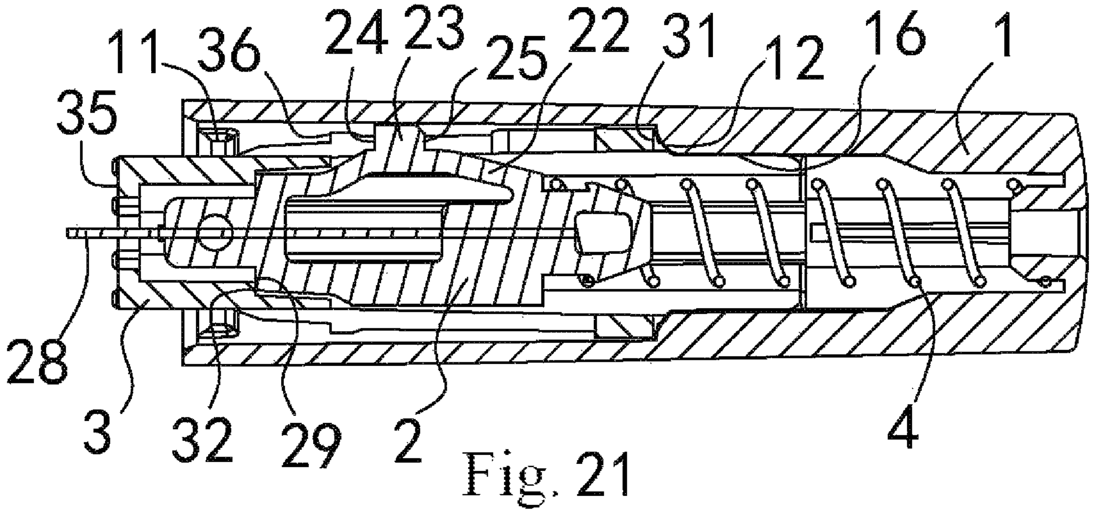
FIG. 21 is a sectional view of the state of ejection for collecting blood in an embodiment of the present invention.

Referring to FIG. 21, after the needle core 2 is unlocked, the launching spring 4 pushes the needle core 2 forward and forces it to eject, until the impact surface 29 at the front end of the needle core 2 hits the third limit surface on the pusher 3 and it stops, completing the blood collection puncture. At this time, the length of the needle tip extending out of the needle-tip puncture hole 34 is the puncture depth or blood collection depth.

7. Stable State after Launching

Figure 22:
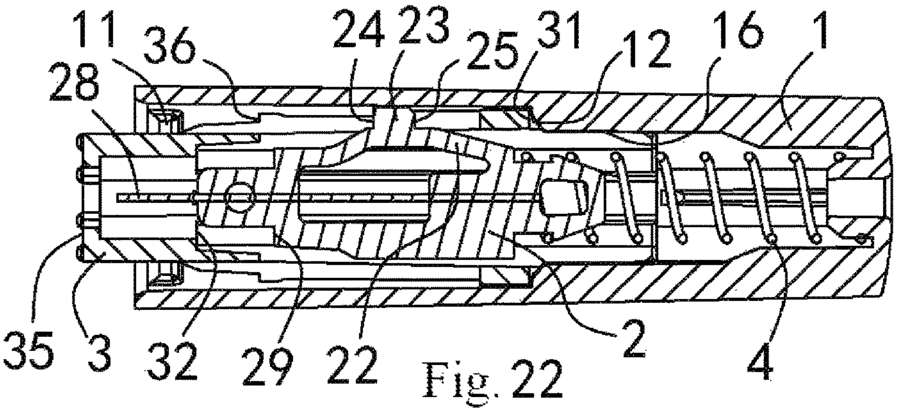
FIG. 22 is a sectional view of the stable state after ejection in an embodiment of the present invention.

Referring to FIG. 22, after launching, the launching spring 4 naturally retracts, driving the needle core 2 to retract, and the needle core 2 is hidden in the steady state inside the housing 1 and the pusher 3.

The process of the embodiment of the present invention in which a false trigger situation occurs in the initial assembly state is as follows:

1. A First Type False Triggering Situation (Triggering the Head of the Pusher 3)

Figure 23:
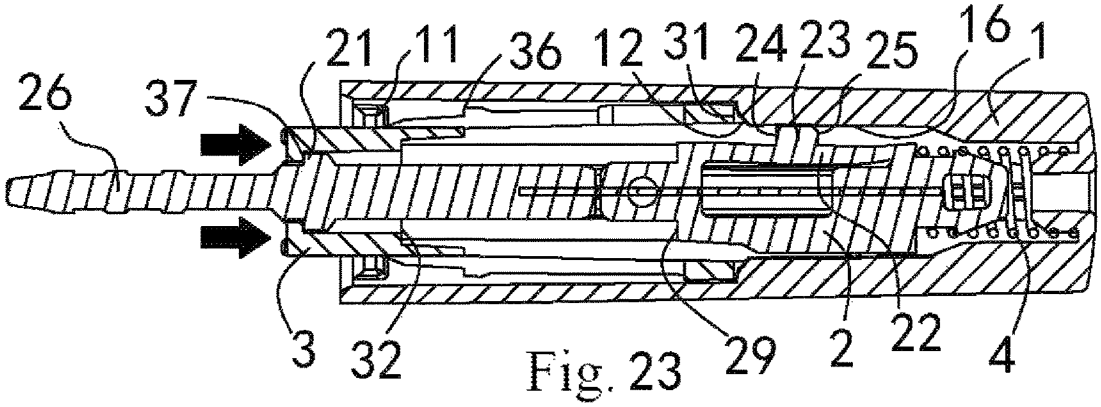
FIG. 23 is a schematic diagram of a first type false triggering situation in an embodiment of the present invention.
Figure 24:
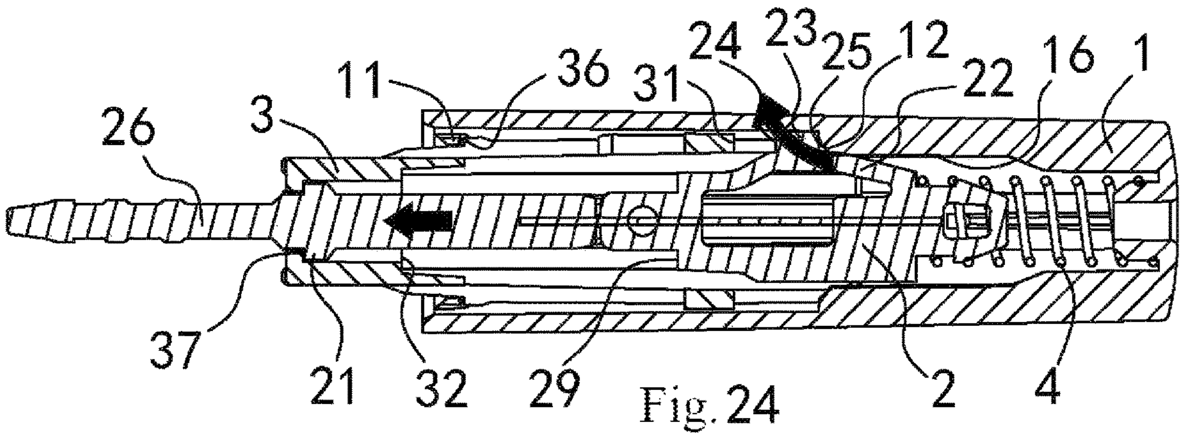
FIG. 24 is a schematic diagram of automatic recovery after a first type false trigger in an embodiment of the present invention.

FIG. 23 is a schematic diagram of the present embodiment in which the first false triggering situation occurs. As can be seen from FIG. 23, when the front end of the pusher 3 is pressed (replaced by an arrow in the figure), the pusher 3 drives needle core 2 to move backwards through the cooperation of the second blocking surface 31 and the protrusion 23 on the needle core 2. At this time, the launching spring 4 is compressed, and the elastic arm 22 on the needle core 2 is bent and deformed inwardly by the influence of the sliding platform 15 on the inner wall of the housing 1. At the same time, the protrusion 23 on the elastic arm 22 is moved backwardly along the triggering surface 12 and slides to the sliding surface 16, until it stops sliding. FIG. 24 shows a schematic diagram of automatic recovery after the first type false triggering in this embodiment. From FIG. 24, it can be seen that when eliminating the triggering force, under the action of the launching spring 4, the protrusion 23 on the elastic arm 22 slides forward along the sliding surface 16 to the position between the second blocking surface 31 and the sliding platform 15, and restores to the initial assembly state.

Figure 25:
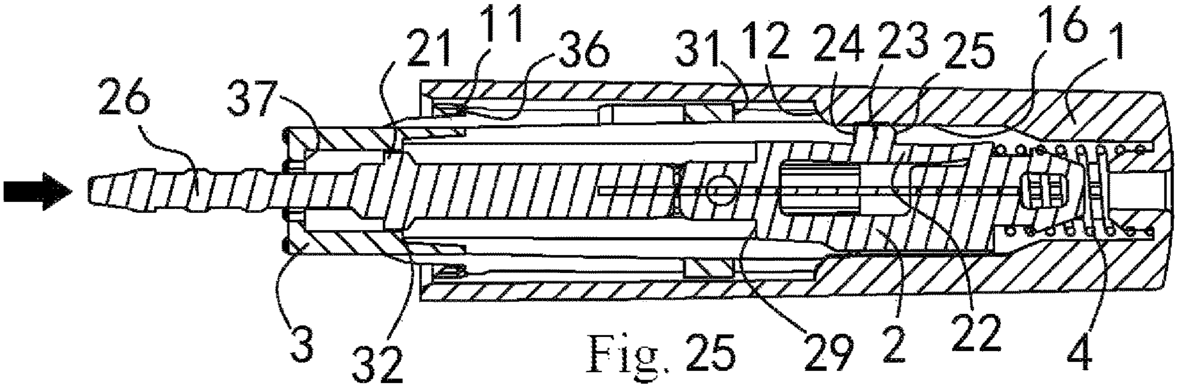
FIG. 25 is a schematic diagram of a second type false triggering situation in the embodiment of the present invention.
Figure 26:
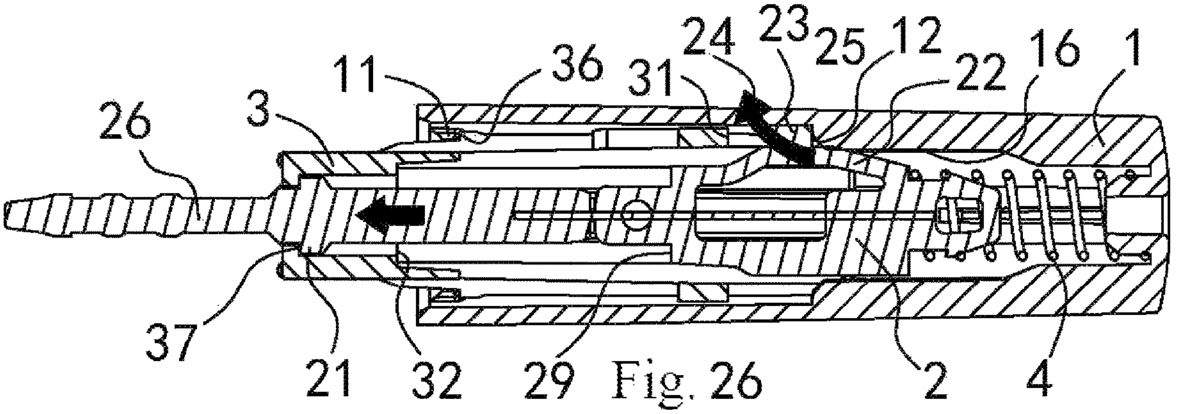
FIG. 26 is a schematic diagram of automatic recovery after a second type false trigger in an embodiment of the present invention.

2. A second type false triggering situation (triggering the head of the protective rod 22) FIG. 25 is a schematic diagram of the second false triggering situation of the present embodiment. As can be seen from FIG. 25, when the front end of the protective rod 26 is pressed (replaced by an arrow in the figure), the needle core 2 is directly driven to move backward, at which time the launching spring 4 is compressed, the elastic arm 22 on the needle core 2 is affected by the sliding platform 15 on the inner wall of the housing 1 to undergo a bending deformation inwardly, and at the same time, the protrusion 23 on the elastic arm 22 slides backwardly along the triggering surface 12 and onto the sliding surface 16, until it stops sliding. FIG. 26 is a schematic diagram of a second type of automatic recovery after false triggering of the present embodiment. As can be seen in FIG. 26, when the triggering force is eliminated, under the action of the launching spring 4, the protrusion 23 on the elastic arm 22 slides forward along the sliding surface 16 to a position between the second blocking surface 31 and the sliding platform 15, and restores to the initial assembly state.

The following descriptions are given for other embodiments of the present invention as well as structural variations:

1. In the above embodiment, the elastic arm 22 is an arch-shaped elastic arm structure, which can be seen from FIG. 7, and both ends of the elastic arm are fixedly connected to the needle core 2. However, the present invention is not limited to this, and a single cantilever structure elastic arm is possible, which is a variation that can be understood and recognized by those skilled in the art. The arch-shaped elastic arm structure is theoretically more elastic compared to the single cantilever structure elastic arm.

2. In the above embodiment, the elastic arm 22 is provided with a protrusion 23, the front end face of the protrusion 23 being a first blocking surface 24 and the rear end face of the protrusion 23 being a resisting surface 25 (see FIG. 13). However, the present invention is not limited to this, for example the elastic arm 22 is provided with two different protrusion structures, the first blocking surface 24 being located on one of the protrusion structures and the resisting surface 25 on the other protrusion structure. Such a design is practically feasible, and this is a variation that will be understood and known to those skilled in the art.

3. In the above embodiment, the elastic arm 22 is provided with a protrusion 23. However, the present invention is not limited thereto, and the elastic arm 22 may be provided without the protrusion 23, which is not a necessary structure for the present invention. For example, it is sufficient to design the elastic arm 22 as a usual cantilever structure, with the rear end face of the cantilever end serving as the first blocking surface 24, and the other side relative to the rear end face of the cantilever serving as the resisting surface 25. This is a variation that will be understood and appreciated by those skilled in the art.

4. In the above embodiment, the sliding surface 16 is a flat surface, which is parallel to the ejection direction of the lancet (see FIG. 13). However, the present invention is not limited to this, the sliding surface 16 may be flat but also be beveled, of course the angle between this beveled surface and the needle body 28 is preferably not too large. It can also be a curved surface, but of course the radius of curvature of the curved surface may not be too small, relatively flat.

5. In the above embodiment, the resisting surface 25 is beveled (see FIGS. 5 and 7). However, the present invention is not limited thereto, and the resisting surface 25 may also be a straight or curved surface. The difference between the straight and beveled surfaces referred to herein is that the former refers to a plane towards the rear of the lancet and the latter refers to a plane that is inclined with respect to the plane.

6. In the above embodiment, the housing 1 is a one-piece molded structure, guiding bevel 14 for guiding the installation of the launching spring 4 is provided on both sides of the rear portion inside the housing 1, and a spring-connecting post 13 for positioning the launching spring 4 is provided at the rear end inside the housing 1. However, the present invention is not limited thereto, which are variations that can be appreciated and understood by those skilled in the art.

Figure 27:
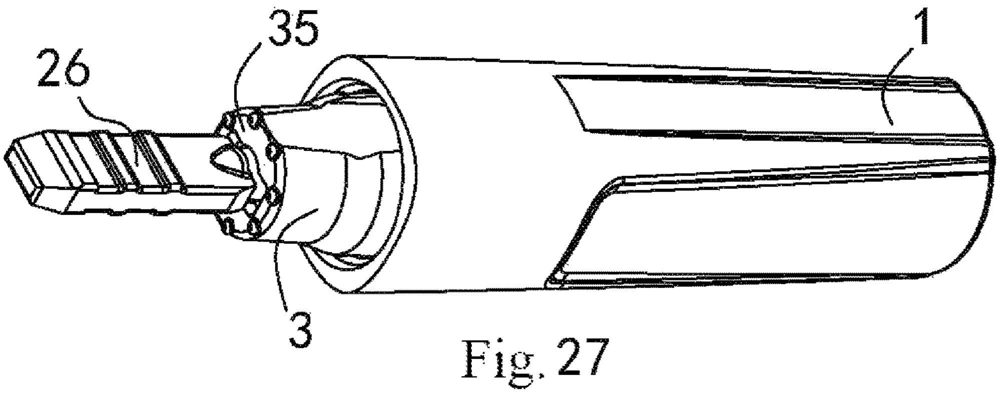
FIG. 27 is a three-dimensional view of a basic type in an embodiment of the present invention.
Figure 28:
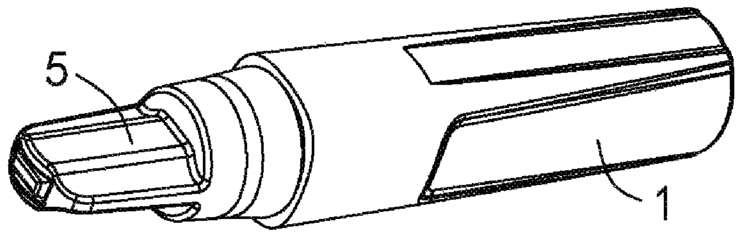
FIG. 28 is a three-dimensional view of a twisted cap type in an embodiment of the present invention.
Figure 29:
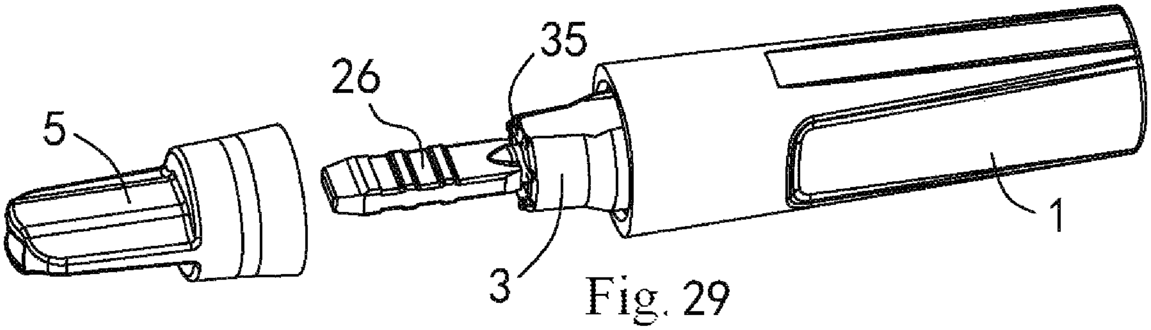
FIG. 29 is a three-dimensional view of the separation state of a twisted cap type in an embodiment of the present invention.

7. In the above embodiment, the four parts of the housing 1, the needle core 2, the pusher 3 and the launching spring 4 can be assembled to form a separate lancet product (see FIG. 27). However, considering that the protective rod 26 is relatively thin and not convenient enough to operate, it is possible to add a twist cap 5 to the head of the lancet, and the twist cap 5 is set on the head of the pusher 3 in the initial assembly state (see FIGS. 28 and 29). It is also possible to add a cover cap to the head of the lancet, the cover cap being set on the head of the pusher 3 in the initially assembly state.

The above embodiments only serve to illustrate the technical concepts and features of the present invention, which are intended to enable persons familiar with the technology to understand the content of the present invention and to implement it accordingly, but not limiting the scope of protection of the present invention in this way. Any equivalent changes or modifications made in accordance with the spirit of the present invention shall be covered by the scope of protection of the present invention.

The invention claimed is:

1. A safety lancet, comprising a housing, a needle core, a pusher and a launching spring, a direction to which a needle tip of the lancet points being defined as a front of the lancet; wherein:

a front end of the needle core is equipped with a protective rod, and a side of the needle core is equipped with an elastic arm;

the elastic arm is provided with a first blocking surface and a resisting surface, the pusher is provided with a second blocking surface, and the second blocking surface cooperates with the first blocking surface to restrict a forward movement of the needle core in relation to the pusher;

a triggering surface is provided on an inner wall of the housing, and the triggering surface cooperates with the resisting surface to force the elastic arm to bend towards a longitudinal axis of the lancet;

a first limiting surface is provided on an outer side of the pusher, a locking bump is provided on the inner wall of the housing, and the locking bump cooperates with the first limiting surface to limit a forward movement of the pusher relative to the housing;

a sliding platform is provided for the resisting surface on the inner wall of the housing, a front end face of the sliding platform is the triggering surface, and a top of the sliding platform forms a sliding surface in a length direction of the lancet;

the second blocking surface has a decoupling point that matches the first blocking surface on the elastic arm, a needle body of the lancet is a center of the lancet in a cross-sectional view, and a distance between the decoupling point and the center is greater than or equal to a distance between the sliding surface and the center;

the protective rod is provided with an obstructing surface, a second limiting surface is provided on an inner wall of the pusher, and the second limiting surface cooperates with the obstructing surface to limit a forward movement of the needle core relative to the pusher.

2. The safety lancet according to claim 1, wherein:

the elastic arm is equipped with a protrusion, a front end face of the protrusion is the first blocking surface, and a rear end face of the protrusion is the resisting surface;

in an initial assembly state of the lancet, the housing is sleeved outside the pusher, a front end of the pusher protrudes out of an opening at a front end of the housing, the needle core is located inside the housing and is slidable relative to the pusher, the protective rod at the front end of the needle core is located inside the pusher, a front end of the protective rod protrudes out of a needle-tip puncture hole at the front end of the pusher, and the launching spring acts in an ejection direction between the needle core and the housing;

in the initial assembly state of the lancet, the second blocking surface of the pusher is located in front of the protrusion of the elastic arm, and the triggering surface on the inner wall of the housing and the sliding surface are located behind the protrusion of the elastic arm, so that the protrusion is located between the second blocking surface and the sliding platform; and when the protective rod or the pusher is accidentally triggered, a triggering force forces the needle core to move backward relative to the housing, compressing the launching spring, while the protrusion on the elastic arm slides backward along the triggering surface to the sliding surface, until it stops sliding, and when the triggering force is eliminated, under an action of the launching spring, the protrusion on the elastic arm slides along the sliding surface forward to a position between the second blocking surface and the sliding platform, restoring the needle core to a position of the needle core in to the initial assembly state of the lancet.

3. The safety lancet according to claim 2, wherein: in the initial assembly state of the lancet, the launching spring is in a pre-compressed state, the pre-compressed state of the launching spring simultaneously forcing the obstructing surface of the protective rod against the second limiting surface of the pusher, and forcing the first limiting surface of the pusher against the locking bump of the housing.

4. The safety lancet according to claim 1, wherein: the sliding surface is a flat surface which is parallel to an ejection direction of the lancet.

5. The safety lancet according to claim 1, wherein: the resisting surface is a straight surface or a beveled surface or a curved surface.

6. The safety lancet according to claim 1, wherein: the needle core is provided with an impact surface, which is oriented towards the front of the lancet, the pusher is provided with a third limiting surface, which is oriented towards a rear of the lancet, and during a launching process of the needle core, the impact surface cooperates with the third limiting surface to limit a puncture depth of the lancet.

7. The safety lancet according to claim 1, wherein: the protective rod includes a stopper that includes the obstructing surface, a notch for the stopper to pass through is provided on the pusher next to a needle-tip puncture hole of the pusher, and in an initial assembly state of the lancet, the notch is located in a rotational position in which the stopper is rotated with the protective rod.

8. The safety lancet according to claim 1, wherein: the elastic arm is of an arch bridge type elastic arm structure.

9. The safety lancet according to claim 1, wherein: a twist cap or cover cap is provided, the twist cap or cover cap being set on a head of the pusher in an initial assembly state of the lancet.

10. The safety lancet according to claim 1, wherein: the housing is a one-piece molded structure, with guiding bevels on both sides of a rear portion of the inside of the housing for guiding installation of the launching spring, and a spring-connecting post for locating the launching spring is provided at a rear end of the housing.

* * * * *